(12) United States Patent
Parthasaradhi Reddy et al.

(10) Patent No.: US 8,921,606 B2
(45) Date of Patent: Dec. 30, 2014

(54) PROCESS FOR CINACALCET HYDROCHLORIDE

(75) Inventors: Bandi Parthasaradhi Reddy, Hyderabad (IN); Kura Rathnakar Reddy, Hyderabad (IN); Dasari Muralidhara Reddy, Hyderabad (IN); Rapolu Raji Reddy, Hyderabad (IN); Jambula Mukunda Reddy, Hyderabad (IN); Bandi Vamsi Krishna, Hyderabad (IN)

(73) Assignee: Hetero Research Foundation, Balanagar, Hyderabad (IN)

( * ) Notice: Subject to any disclaimer, the term of this patent is extended or adjusted under 35 U.S.C. 154(b) by 0 days.

(21) Appl. No.: 13/810,319

(22) PCT Filed: Jul. 16, 2010

(86) PCT No.: PCT/IN2010/000477
§ 371 (c)(1),
(2), (4) Date: Jan. 15, 2013

(87) PCT Pub. No.: WO2012/007954
PCT Pub. Date: Jan. 19, 2012

(65) Prior Publication Data
US 2013/0178654 A1    Jul. 11, 2013

(51) Int. Cl.
| C07C 45/41 | (2006.01) |
| C07C 209/70 | (2006.01) |
| C07C 209/84 | (2006.01) |
| C07C 209/28 | (2006.01) |

(52) U.S. Cl.
CPC ............ *C07C 45/41* (2013.01); *C07C 209/70* (2013.01); *C07C 209/28* (2013.01); *C07C 209/84* (2013.01)
USPC ......................................... 568/435; 564/387

(58) Field of Classification Search
USPC .......................................... 568/435; 564/387
See application file for complete search history.

(56) References Cited

U.S. PATENT DOCUMENTS

| 6,211,244 B1 * | 4/2001 | Van Wagenen et al. ...... 514/649 |
| 7,250,533 B2 * | 7/2007 | Lifshitz-Liron et al. ...... 564/336 |
| 2010/0174119 A1 * | 7/2010 | Ducry et al. ................... 568/420 |

FOREIGN PATENT DOCUMENTS

| EP | 1990333 A1 | 11/2008 |
| WO | WO-2007/127445 A2 | 11/2007 |
| WO | WO-2008/035212 A2 | 3/2008 |
| WO | WO-2008/035381 A2 | 3/2008 |
| WO | WO2008035212 A2 * | 3/2008 |
| WO | WO-2008/058235 A2 | 5/2008 |
| WO | WO-2008/068625 A2 | 6/2008 |
| WO | WO-2008/117299 A1 | 10/2008 |
| WO | WO-2009/153814 A1 | 12/2009 |

OTHER PUBLICATIONS

Wang et al. Synthesis of Cinacalcet congers. Tetrahedron Letters 45 (2004), 8355-8358.*
Bijukumar et al., Efficient Synthesis of Cinacalcet Hydrochloride, Synthetic Communications, 38(10): 1512-1517 (2008).
Lednicer, Synthesis and Antifertility Activity of 4- and 5-(omega-arylalkyl) orazolidinethiones, Journal of Medicinal Chemistry, 11: 1258-1262 (1968).
Sorbera et al., Cinacalcet Hydrochloride, Drugs of the Future, 27(9): 831-836 (2002).
Thiel et al., Practical Synthesis of the Calcimimetic Agent, Cinacalcet, Tetrahedron Letters, 49(1): 13-15 (2008).
Wang et al., Synthesis of Cinacalcet congers, Tetrahedron Letters, 45: 8355-8358 (2004).
International Search Report PCT/IN10/00477, 1 page (mailed Apr. 25, 2011).
Written Opinion PCT/IN10/00477, 5 pages (mailed Apr. 25, 2011).

* cited by examiner

*Primary Examiner* — Sikarl Witherspoon
(74) *Attorney, Agent, or Firm* — Choate Hall & Stewart LLP; Charles E. Lyon; Thomas H. McLean

(57) ABSTRACT

3-[3-(Trifluoromethyl)phenyl]propionaldehyde is a key intermediate for the preparation of cinacalcet hydrochloride. The present invention provides a novel process for the preparation of 3-[3-(trifluoromethyl)phenyl]propionaldehyde. The present invention also provides an improved process for preparation of cinacalcet hydrochloride in high yields. The present invention further provides a process for purification of cinacalcet hydrochloride.

20 Claims, No Drawings

PROCESS FOR CINACALCET HYDROCHLORIDE

FIELD OF THE INVENTION

3-[3-(Trifluoromethyl)phenyl]propionaldehyde is a key intermediate for the preparation of cinacalcet hydrochloride. The present invention provides a novel process for the preparation of 3-[3-(trifluoromethyl)phenyl]propionaldehyde. The present invention also provides an improved process for preparation of cinacalcet hydrochloride in high yields. The present invention further provides a process for purification of cinacalcet hydrochloride.

BACKGROUND OF THE INVENTION

Cinacalcet hydrochloride is chemically, (R)-α-methyl-N-[3-[3-trifluoromethyl)phenyl]propyl]-1-napthalenemethanamine hydrochloride. Cinacalcet hydrochloride is represented by the following structure:

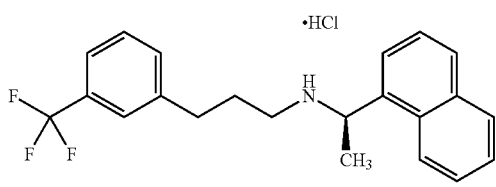 [SMILES: Cl ; C[C@@H](NCCCc1cccc(C(F)(F)F)c1)c1cccc2ccccc12]

Calcimimetics are a class of orally active, small molecules that decrease the secretion of parathyroid hormone ("PTH") by activating calcium receptors. The secretion of PTH is normally regulated by the calcium-sensing receptor. Calcimimetic agents increase the sensitivity of this receptor to calcium, which inhibits the release of parathyroid hormone, and lowers parathyroid hormone levels within a few hours. Calcimimetics are used to treat hyperparathyroidism, a condition characterized by the over-secretion of PTH that results when calcium receptors on parathyroid glands fail to respond properly to calcium in the bloodstream. Elevated levels of PTH, an indicator of secondary hyperparathyroidism, are associated with altered metabolism of calcium and phosphorus, bone pain, fractures, and an increased risk for cardiovascular death.

Cinacalcet hydrochloride is approved for treatment of secondary hyperparathyroidism in patients with chronic kidney disease on dialysis. Treatment with cinacalcet hydrochloride lowers serum levels of PTH as well as the calcium/phosphorus ion product, a measure of the amount of calcium and phosphorus in the blood. Cinacalcet hydrochloride is marketed as Sensipar® in USA and as Mimpara® in Europe.

Cinacalcet and its pharmaceutical acceptable salts were disclosed in U.S. Pat. No. 6,211,244 (herein after referred to as the '244 patent). In accordance with the '244 patent, cinacalcet can prepared by reacting 1-acethylnaphthalene with 3-[3-(trifloromethyl)phenyl]propylamine in the presence of titanium isopropoxide to produce an cinacalcet isoimine, followed by treatment with sodium cyanoborohydride in methanol and resolution of the racemic cinacalcet base by chiral liquid chromatography. The synthetic procedure is illustrated in scheme I, below:

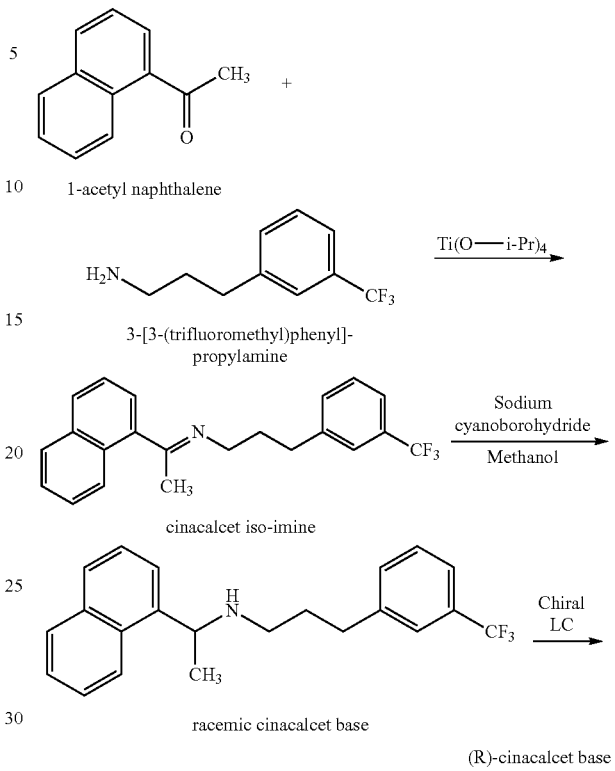

According to the '244 patent, cinacalcet can be prepared by reacting 3-fluoromethylcinnamonitrile with diisobutyl aluminum hydride to give aluminum-imine intermediate, which was then reacted with (R)-1-(1-naphthyl)ethylamine, and reducing the cinacalcet imine intermediate thus obtained with sodium cyanoborohydride in ethanol.

Process for the preparation of cinacalcet was reported in *Drug of the future*, 2002, 27(9), 831-836. According to the journal, cinacalcet can be prepared by reacting (R)-(1-naphthyl)ethylamine with 3-[3-(trifluoromethyl)phenyl]propionaldehyde in the presence of titanium tetraisopropoxide to give cinacalcet imine, which was then reduced with sodium cyanoborohydride in ethanol. The synthetic procedure was illustrated in scheme II, below:

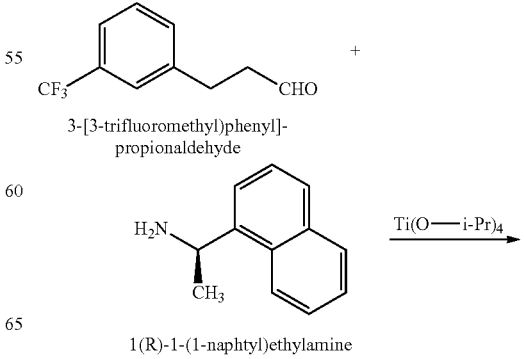

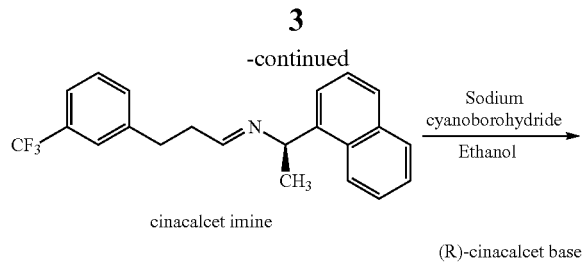

cinacalcet imine (R)-cinacalcet base

Process for the preparation of 3-[3-(trifluoromethyl)phenyl]propionaldehyde was reported in *Tetrahedron letters*, (45), 8355-8358, (2004) *footnote* 12. According to the journal, 3-[3-(trifluoromethyl)phenyl]propionaldehyde can be prepared by reduction of 3-(trifluoromethyl)cinnamic acid to the corresponding alcohol followed by swern oxidation to give the desired aldehyde. The synthetic procedure was illustrated in scheme III, below:

Scheme III

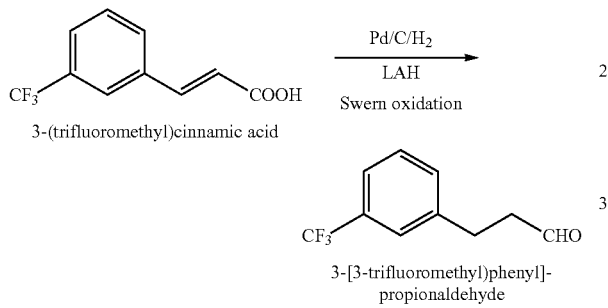

3-(trifluoromethyl)cinnamic acid

3-[3-trifluoromethyl)phenyl]-propionaldehyde

PCT publication WO 2008/035212 disclosed a process for preparing 3-[3-(trifluoromethyl)phenyl]propionaldehyde. According to the publication, 3-[3-(trifluoromethyl)phenyl]propionaldehyde can be prepared by reacting 3-[3-(trifluoromethyl)phenyl]propan-1-ol with 2,2,6,6-tetramethylpiperidine-1-oxyl (TEMPO) and sodium hypochlorite in the presence of potassium bromide in methylene chloride.

PCT publication WO 2008/068625 disclosed a process for the preparation of cinacalcet by reductive amination of 3-(3-trifluoromethylphenyl)propanal with (R)-1-naphthylethylamine in the presence of a sodium triacetoxyborohydride.

PCT publication WO 2007/127445 disclosed a process for the preparation of cinacalcet by reacting 3-(3-trifluoromethylphenyl)propanoic acid with R)-1-naphthylethylamine to give N-[(1R)-1-(1-napthyl)ethyl]-3-(3-trifluoromethyl)phenyl]propanamide, which was then reduced to give cinacalcet and its pharmaceutically acceptable salts. Similar process was also described in PCT publications WO 2008/035381, WO 2008/058235, WO 2008/117299; *Tetrahedron Letters* 2008 49(1), 13-15 and *Synthetic communications* 2008 38(10), 1512-1517.

PCT publication WO 2009/153814 disclosed a process for the preparation of cinacalcet. According to the publication, cinacalcet can be prepared by reacting (R)-1-naphthylethylamine with 3-(3-trifluoromethylphenyl)propenaldehyde to give the non isolated (R)-N-[3-[3-(trifluoromrthyl)phenyl]-2-propenylimino-N-[1-(1-napththyl)ethylamine, which was then reduced with sodium borohydride in methanol and hydrogenating the cinacalcet imine intermediate thus obtained.

3-[3-(Trifluoromethyl)phenyl]propionaldehyde is a key intermediate for the preparation of cinacalcet hydrochloride.

The major problem with the direct preparation of the 3-[3-(trifluoromethyl)phenyl]propionaldehyde from an ester of 3-[3-(trifluoromethyl)phenyl]propionic acid is that the question of reproducibility of the aldehyde formation when used the reagents such as oxalyl chloride. Another problem with this conversation is that the over reduction of the aldehyde formed to the corresponding undesired alcohol. The present invention makes now available a more efficient process for the manufacture of cinacalcet hydrochloride in particular by providing efficient manufacture of 3-[3-(trifluoromethyl)phenyl]propionaldehyde. According to the present invention, 3-[3-(trifluoromethyl)phenyl]propionaldehyde can prepared from ester of 3-[3-(trifluoromethyl)phenyl]propionic acid in a single step. It has been found that the ester of 3-[3-(trifluoromethyl)phenyl]propionic acid can be reduced selectively to the corresponding aldehyde by choosing suitable reaction condition, avoiding the formation of excess of the undesired corresponding alcohol.

2-[3-(Trifluoromethyl)phenyl]-5-[3-(trifluoromethyl)phenyl]-3-hydroxy pentanal and (R)-1-(naphthyl)ethylamine are potential impurities in cinacalcet hydrochloride.

The chemical formula of (R)-1-(naphthyl)ethylamine may be represented as:

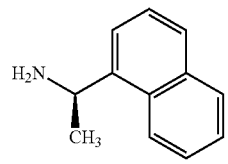

The chemical formula of 2-[3-(trifluoromethyl)phenyl]-5-[3-(trifluoromethyl)phenyl]-3-hydroxy pentanal may be represented as:

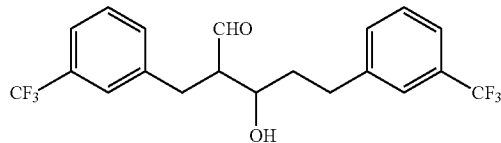 [SMILES: O=CC(Cc1cccc(C(F)(F)F)c1)C(O)CCc1cccc(C(F)(F)F)c1]

The present invention is intended to enhance the purity of cinacalcet hydrochloride. In particular, the present invention is directed to reduce or remove 2-[3-(trifluoromethyl)phenyl]-5-[3-(trifluoromethyl)phenyl]-3-hydroxy pentanal and (R)-1-(naphthyl)ethylamine impurities from cinacalcet hydrochloride.

Thus, one object of the present invention is to provide a novel process for the preparation of 3-[3-(trifluoromethyl)phenyl]propionaldehyde.

Another object of the present invention is to provide an improved process for the preparation of cinacalcet hydrochloride.

Yet another object of the present invention is to provide a process for the purification of cinacalcet hydrochloride.

SUMMARY OF THE INVENTION

In one aspect, the present invention provided a novel process for the preparation of 3-[3-(trifluoromethyl)phenyl]propionaldehyde of formula I,

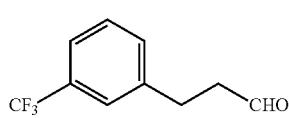

I which comprises, reducing the methyl 3-[3-(trifluoromethyl)phenyl]propanoate of formula II

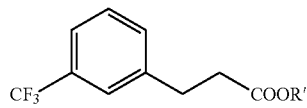

II wherein R' is lower alkyl.
with diisobutylaluminium hydride (DIBAL-H) in an hydrocarbon solvent, an chlorinated solvent, an ether solvent or mixtures thereof below −40° C. to obtain a compound of formula I.

In another aspect, the present invention provided a novel process for the preparation of 3-[3-(trifluoromethyl)phenyl]propionaldehyde, which comprises:

a) reducing the methyl 3-[3-(trifluoromethyl)phenyl]propanoate with diisobutylaluminium hydride (DIBAL-H) in an hydrocarbon solvent, an chlorinated solvent, an ether solvent or mixtures thereof below −40° C.;

b) quenching the reaction mass with an alcohol solvent;

c) adding ethyl acetate to the reaction mass obtained in step (b);

d) separating out the solids; and e) isolating 3-[3-(trifluoromethyl)phenyl]propionaldehyde from the mother liquor.

In another aspect, the present invention provided an improved process for the preparation of cinacalcet hydrochloride in high yields, which comprises:

a) adding 3-[3-(trifluoromethyl)phenyl]propionaldehyde to (R)-(1-naphthyl)ethylamine in ether solvent in the presence of titanium(IV)isopropoxide below −5° C.;

b) reacting sodium cyanoborohydride with the reaction mass obtained in step (a);

c) concentrating the reaction mass;

d) adding ether solvent, hydrochloride in an organic solvent and water to the residual mass obtained in step (c); and e) isolating cinacalcet hydrochloride.

Yet another aspect, the present invention provided a process for the purification of cinacalcet hydrochloride, which comprises:

a) stirring cinacalcet hydrochloride with a solvent system comprising water and solvent selected from alcohol solvent, nitrile solvent and mixture thereof; and b) isolating substantially pure cinacalcet hydrochloride.

DETAILED DESCRIPTION OF THE INVENTION

The term "room temperature" refers to temperature at about 25 to 35° C.

According to one aspect of the present invention, there is provided a novel process for the preparation of 3-[3-(trifluoromethyl)phenyl]propionaldehyde of formula I,

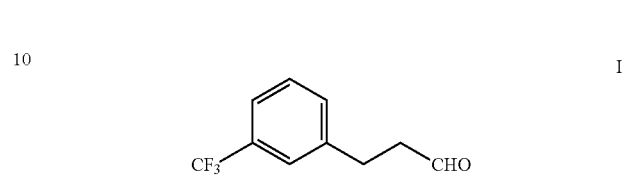

I which comprises, reducing the methyl 3-[3-(trifluoromethyl)phenyl]propanoate of formula II

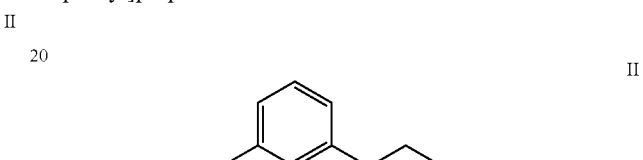

II wherein R' is lower alkyl.
with diisobutylaluminium hydride (DIBAL-H) in an hydrocarbon solvent, an chlorinated solvent, an ether solvent or mixtures thereof below −40° C. to obtain a compound of formula I.

The term "lower alkyl" refers to $C_1$-$C_4$ alkyl. Preferably alkyl may be selected from methyl or ethyl, and more preferable alkyl is methyl.

The solvent used in the process may preferably be selected from the group consisting of cyclohexane, cyclohexene, cycloheptane, cyclopentane, n-hexane, n-heptane, benzene, toluene, xylene, dichloromethane, chloromethane, dichloroethane, chloroform, carbon tetrachloride, chlorobenzene, tetrahydrofuran, diisopropyl ether, tertrahydropyran, 1,4-dioxane, methyl tert-butyl ether, ethyl tert-butyl ether, diethyl ether, di-tert-butyl ether, diglyme, dimethoxyethane, dimethoxymethane and methoxyethane. More preferable solvents are n-hexane, cyclohexane, toluene, dichloromethane, diisopropyl ether and tetrahydrofuran, and still more preferable solvents are n-hexane, toluene, dichloromethane and tetrahydrofuran.

The reaction mass may preferably be maintained in the process below −50° C. and more preferable at about −70 to −85° C.

According to another aspect of the present invention, there is provided a novel process for the preparation of 3-[3-(trifluoromethyl)phenyl]propionaldehyde, which comprises:

a) reducing the methyl 3-[3-(trifluoromethyl)phenyl]propanoate with diisobutylaluminium hydride (DIBAL-H) in an hydrocarbon solvent, an chlorinated solvent, an ether solvent or mixtures thereof below −40° C.;

b) quenching the reaction mass with an alcohol solvent;

c) adding ethyl acetate to the reaction mass obtained in step (b);

d) separating out the solids; and e) isolating 3-[3-(trifluoromethyl)phenyl]propionaldehyde from the mother liquor.

The solvent used in step (a) may preferably be selected from the group consisting of cyclohexane, cyclohexene, cycloheptane, cyclopentane, n-hexane, n-heptane, benzene, toluene, xylene, dichloromethane, chloromethane, dichloroethane, chloroform, carbon tetrachloride, chlorobenzene, tetrahydrofuran, diisopropyl ether, tertrahydropyran, 1,4-dioxane, methyl tert-butyl ether, ethyl tert-butyl ether, diethyl ether, di-tert-butyl ether, diglyme, dimethoxyethane, dimethoxymethane and methoxyethane. More preferable solvents are n-hexane, cyclohexane, toluene, dichloromethane, diisopropyl ether and tetrahydrofuran, and still more preferable solvents are n-hexane, toluene, dichloromethane and tetrahydrofuran.

The reaction mass may preferably be maintained in step (a) below −50° C. and more preferable at about −70 to −85° C.

The alcohol solvent used in step (b) may preferably be a solvent or mixture of solvents selected from methanol, ethanol, isopropyl alcohol, isobutanol and n-butanol, and more preferable alcohol solvent is methanol.

The separated solids may be collected by the method known such as centrifugation or filtration.

Isolation of 3-[3-(trifluoromethyl)phenyl]propionaldehyde in step (e) can be performed by conventional methods such as cooling, removal of solvents, concentrating to the reaction mass, adding an anti-solvent, extraction with a solvent and the like.

According to another aspect of the present invention, there is provided an improved process for the preparation of cinacalcet hydrochloride in high yields, which comprises:
  a) adding 3-[3-(trifluoromethyl)phenyl]propionaldehyde to (R)-(1-naphthyl)ethylamine in ether solvent in the presence of titanium(IV)isopropoxide below −5° C.;
  b) reacting sodium cyanoborohydride with the reaction mass obtained in step (a);
  c) concentrating the reaction mass;
  d) adding ether solvent, hydrochloride in an organic solvent and water to the residual mass obtained in step (c); and
  e) isolating cinacalcet hydrochloride.

The ether solvent used in step (a) may preferably be a solvent or mixture of solvents selected from tetrahydrofuran, diisopropyl ether, tertrahydropyran, 1,4-dioxane, methyl tert-butyl ether, ethyl tert-butyl ether, diethyl ether, di-tert-butyl ether, diglyme, dimethoxyethane, dimethoxymethane and methoxyethane, and more preferable ether solvents are tetrahydrofuran and diisopropyl ether.

The reaction in step (a) may preferably be carried out at below −20° C. and more preferable at about −30 to −60° C.

Preferably the reaction mass is concentrated in step (c) by distilling off the solvent. The distilling off the solvent may be carried out at atmospheric pressure or at reduced pressure. The distillation may preferably be carried out until the solvent is almost completely distilled off.

The ether solvent used in step (d) may preferably be a solvent or mixture of solvents selected from tetrahydrofuran, diisopropyl ether, tertrahydropyran, 1,4-dioxane, methyl tert-butyl ether, ethyl tert-butyl ether, diethyl ether, di-tert-butyl ether, diglyme, dimethoxyethane, dimethoxymethane and methoxyethane, and more preferable ether solvents are tetrahydrofuran and diisopropyl ether.

The organic solvent used in step (d) may preferably be a solvent or mixture of solvents selected from the group consisting of an ether solvents such as tetrahydrofuran, diisopropyl ether, tertrahydropyran, 1,4-dioxane, methyl tert-butyl ether, ethyl tert-butyl ether, diethyl ether, di-tert-butyl ether, diglyme, dimethoxyethane, dimethoxymethane and methoxyethane; an ester solvents such as ethyl acetate, methyl acetate, isopropyl acetate, tert-butyl methyl acetate and ethyl formate. More preferable organic solvents are diisopropyl ether and ethyl acetate, still more preferable organic solvent is ethyl acetate.

Cinacalcet hydrochloride may be isolated in step (e) by methods known such as filtration or centrifugation.

According to another aspect of the present invention, there is provides a process for the purification of cinacalcet hydrochloride, which comprises:
  a) stirring cinacalcet hydrochloride with a solvent system comprising water and solvent selected from alcohol solvent, nitrile solvent and mixture thereof; and
  b) isolating substantially pure cinacalcet hydrochloride.

The term "substantially pure cinacalcet hydrochloride" refers to cinacalcet hydrochloride having the purity greater than about 98% by weight, preferably greater than about 99% by weight, and more preferably greater than about 99.5% by weight.

The alcohol solvent used in step (a) may preferably be selected from methanol, ethanol, isopropyl alcohol, isobutanol or n-butanol, and more preferable alcohol solvent is methanol.

The nitrile solvent used in step (a) may preferably be selected from acetonitrile, propionitrile, butyronitrile or benzonitrile, and more preferable nitrile solvent is acetonitrile.

The step (a) is preferably carried out at elevated temperature. The term "elevated temperature" refers to temperature at above 25° C. More preferably the step (a) is carried out at about 40 to 100° C. and still more preferably at about 45 to 90° C.

Isolation of highly pure cinacalcet hydrochloride may preferably be carried out by methods known such as filtration or centrifugation.

The purification process yields cinacalcet hydrochloride with reduced levels of impurities, specifically, 2-[3-(trifluoromethyl)phenyl]-5-[3-(trifluoromethyl)phenyl]-3-hydroxy pentanal and (R)-1-(naphthyl)ethylamine.

The purity of cinacalcet hydrochloride is measured by High performance liquid chromatography (HPLC).

The invention will now be further described by the following examples, which are illustrative rather than limiting.

EXAMPLES

Example 1

Preparation of
3-[3-(trifluoromethyl)phenyl]propionic acid

Palladium carbon (10%, 6 gm) was added to water (20 ml) and then added 3-(trifluoromethyl)cinnamic acid (100 gm) and toluene (1000 ml). The resulting contents were hydrogenated with hydrogen gas at a pressure of 4 kg at 45 to 50° C. for 2 hour 30 minutes. The reaction mass was then filtered through celite bed and the layers were separated. The organic layer was dried over sodium sulfate and the solvent was distilled off under reduced pressure to obtain 98.7 gm of 3-[3-(trifluoromethyl)phenyl]propionic acid.

Example-2

Preparation of methyl
3-[3-(trifluoromethyl)phenyl]propanoate

3-[3-(Trifluoromethyl)phenyl]propionic acid (100 gm) as obtained in example 1 was dissolved in methanol (250 ml) and then added concentrated sulfuric acid (45 gm) slowly for 25 minutes. The temperature of the reaction mass was raised to 40 to 45° C. and maintained for 1 hour at 30 to 45° C. The methanol solvent was distilled off under vacuum at below 45° C. to obtain residual mass. To the residual mass was added water (600 ml) and methylene dichloride (500 ml). The separated organic layer was dried over sodium sulfate and the solvent was distilled off under reduced pressure to obtain 99.2 gm of methyl 3-[3-(trifluoromethyl)phenyl]propanoate.

Example-3

Preparation of
3-[3-(trifluoromethyl)phenyl]propionaldehyde

Methyl 3-[3-(trifluoromethyl)phenyl]propanoate (5 gm) as obtained in example 2 was added to toluene (50 ml) and then cooled to −75 to −80° C. To the solution was added a solution of diisobutylaluminium hydride (4.59 gm) in n-hexane (33 ml) slowly for 1 hour 30 minutes at −75 to −80° C. The reaction mass was maintained for 1 hour at −75 to −80° C. and then added methanol (5 ml) at −75 to −80° C. The temperature of the reaction mass was raised to 0° C. and the reaction mass was poured to the chilled water (150 ml). To the reaction mass was added ethyl acetate (50 ml) and then added sodium sulfate solution (20%, 25 ml). The reaction mass was maintained for 1 hour 30 minutes at room temperature and then filtered through celite bed. The layers were separated and the aqueous layer was extracted with toluene. The combined organic layer was dried over sodium sulfate and the solvent was distilled off under reduced pressure to obtain 4.2 gm of 3-[3-(trifluoromethyl)phenyl]propionaldehyde.
3-[3-(Trifluoromethyl)phenyl]propionaldehyde: 99.2%;
3-[3-(Trifluoromethyl)phenyl]propanol impurity: 0.3%.

Example 4

Preparation of Cinacalcet Hydrochloride

3-[3-(Trifluoromethyl)phenyl]propionaldehyde (14.2 gm) as obtained in example 3 was dissolved in tetrahydrofuran (50 ml) and then cooled to −45 to −50° C. To the solution was added a solution of (R)-(1-naphthyl)ethylamine (10 gm) in tetrahydrofuran (150 ml) at −45 to −50° C. slowly for 2 hours 30 minutes and then added titanium(IV)isopropoxide (4.1 gm). The reaction mass was stirred for 15 minutes at −45 to −50° C. and then added a solution of sodium cyanoborohydride (4 gm) in methanol (40 ml) slowly for 20 minutes. The temperature of the reaction mass was raised to room temperature and maintained for 2 hours at room temperature. To the reaction mass was added water (50 ml) and the reaction mass was then filtered through celite bed. The layers were separated and the aqueous layer was extracted with diisopropyl ether. The combined organic layer was dried and the solvent was distilled off under reduced pressure to obtain residual mass. To the residual mass was added diisopropyl ether (80 ml) and water (100 ml), and then heated to 55 to 60° C. Hydrochloride in diisopropyl ether (16% HCl, 12.5 ml) was added to the reaction mass at 55 to 60° C. and maintained for 30 minutes at 55 to 60° C. The reaction mass was cooled to room temperature and maintained for 15 hours at room temperature. The separated solid was filtered and dried to obtain 18 gm of cinacalcet hydrochloride.
Cinacalcet hydrochloride: 98.5%;
2-[3-(Trifluoromethyl)phenyl]-5-[3-(trifluoromethyl)phenyl]-3-hydroxy pentanal impurity: 1.08%;
(R)-1-(Naphthyl)ethylamine impurity: 0.32%.

Example 5

Preparation of Cinacalcet Hydrochloride

3-[3-(Trifluoromethyl)phenyl]propionaldehyde (7.07 gm) was dissolved in tetrahydrofuran (25 ml) and then cooled to −45 to −50° C. To the solution was added a solution of (R)-(1-naphthyl)ethylamine (5 gm) in tetrahydrofuran (75 ml) at −45 to −50° C. slowly for 2 hours 30 minutes and then added titanium(IV)isopropoxide (2.07 gm). The reaction mass was stirred for 20 minutes at −45 to −50° C. and then added a solution of sodium cyanoborohydride (2 gm) in methanol (20 ml) slowly for 20 minutes. The temperature of the reaction mass was raised to room temperature and maintained for 2 hours at room temperature. To the reaction mass was added water (25 ml) and the reaction mass was then filtered through celite bed. The layers were separated and the aqueous layer was extracted with diisopropyl ether. The combined organic layer was dried over sodium sulfate and the solvent was distilled off under reduced pressure to obtain residual mass. To the residual mass was added diisopropyl ether (40 ml) and water (50 ml). The contents were heated to 55 to 60° C. Hydrochloride in ethyl acetate (16% HCl, 6.2 ml) was added to the reaction mass at 55 to 60° C. and maintained for 30 minutes at 55 to 60° C. The reaction mass was cooled to room temperature and maintained for 15 hours at room temperature, filtered. The solid obtained was dried to obtain 9.5 gm of cinacalcet hydrochloride.
Cinacalcet hydrochloride: 98.6%;
2-[3-(Trifluoromethyl)phenyl]-5-[3-(trifluoromethyl)phenyl]-3-hydroxy pentanal impurity: 1.05%;
(R)-1-(Naphthyl)ethylamine impurity: 0.3%.

Example 6

Preparation of Cinacalcet Hydrochloride

3-[3-(Trifluoromethyl)phenyl]propionaldehyde (142 gm) was dissolved in diisopropyl ether (500 ml) and then cooled to −45 to −50° C. To the solution was added a solution of (R)-(1-naphthyl)ethylamine (100 gm) in diisopropyl ether (1400 ml) at −45 to −50° C. slowly for 2 hours 30 minutes and then added titanium(IV)isopropoxide (41 gm). The reaction mass was stirred for 15 minutes at −45 to −50° C. and then added a solution of sodium cyanoborohydride (40 gm) in methanol (380 ml) slowly for 20 minutes. The temperature of the reaction mass was raised to room temperature and maintained for 2 hours at room temperature. To the reaction mass was added water (450 ml) and the reaction mass was then filtered through celite bed. The layers were separated and the aqueous layer was extracted with diisopropyl ether. The combined organic layer was dried and the solvent was distilled off under reduced pressure to obtain residual mass. To the residual mass was added diisopropyl ether (700 ml) and water (1000 ml). The contents were heated to 55 to 60° C. Hydrochloride in diisopropyl ether (16% HCl, 125 ml) was added to the reaction mass at 55 to 60° C. and maintained for 30 minutes at 55 to 60° C. The reaction mass was cooled to room temperature and maintained for 15 hours at room temperature, filtered. The solid was dried to obtain 175 gm of cinacalcet hydrochloride.
Cinacalcet hydrochloride: 98.5%;
2-[3-(Trifluoromethyl)phenyl]-5-[3-(trifluoromethyl)phenyl]-3-hydroxy pentanal impurity: 1.08%;
(R)-1-(Naphthyl)ethylamine impurity: 0.32%.

Example 7

Purification of Cinacalcet Hydrochloride

Cinacalcet hydrochloride (10 gm) as obtained in example 4 was dissolved in a mixture of water (125 ml) and methanol (15 ml). The reaction mass was stirred for 1 hour at room temperature and filtered. The solid obtained was dried at 60 to 65° C. for 6 hours to obtain 9.2 gm of substantially pure cinacalcet hydrochloride.

Cinacalcet hydrochloride: 99.96%;
2-[3-(Trifluoromethyl)phenyl]-5-[3-(trifluoromethyl)phenyl]-3-hydroxy pentanal impurity: Not detected;
(R)-1-(Naphthyl)ethylamine impurity: Not detected.

Example 8

Purification of Cinacalcet Hydrochloride

Cinacalcet hydrochloride (10 gm) was suspended in a mixture of water (80 ml) and acetonitrile (20 ml). The contents were heated to 80° C. and stirred for 20 minutes at 80° C. to obtain solution. The solution was cooled to at room temperature and maintained for 2 hours. The separated solid was filtered and dried to obtain 8.3 gm of substantially pure cinacalcet hydrochloride.

Cinacalcet hydrochloride: 99.6%;
2-[3-(Trifluoromethyl)phenyl]-5-[3-(trifluoromethyl)phenyl]-3-hydroxy pentanal impurity: Not detected;
(R)-1-(Naphthyl)ethylamine impurity: 0.11%.

Example 9

Purification of Cinacalcet Hydrochloride

Cinacalcet hydrochloride (10 gm) was dissolved in methanol (15 ml). To the solution was added water (125 ml) slowly for 40 minutes to form precipitation. The reaction mass was stirred for 2 hour at room temperature and filtered. The solid obtained was dried to obtain 9.3 gm of substantially pure cinacalcet hydrochloride.

Cinacalcet hydrochloride: 99.98%;
2-[3-(Trifluoromethyl)phenyl]-5-[3-(trifluoromethyl)phenyl]-3-hydroxy pentanal impurity: Not detected;
(R)-1-(Naphthyl)ethylamine impurity: Not detected.

We claim:

1. A process for the preparation of 3-[3-(trifluoromethyl)phenyl]propionaldehyde of formula I,

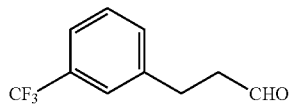

which comprises, reducing methyl 3-[3-(trifluoromethyl)phenyl]propanoate of formula II

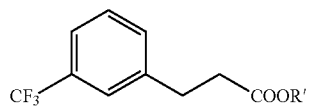

wherein R' is lower alkyl,
with diisobutylaluminium hydride (DIBAL-H) in an hydrocarbon solvent, an chlorinated solvent, an ether solvent or mixtures thereof below −40° C. to obtain a compound of formula I.

2. The process according to claim 1, wherein the R' is methyl or ethyl.

3. The process according to claim 1, wherein the solvent used in the process is selected from the group consisting of cyclohexane, cyclohexene, cycloheptane, cyclopentane, n-hexane, n-heptane, benzene, toluene, xylene, dichloromethane, chloromethane, dichloroethane, chloroform, carbon tetrachloride, chlorobenzene, tetrahydrofuran, diisopropyl ether, tertrahydropyran, 1,4-dioxane, methyl tert-butyl ether, ethyl tert-butyl ether, diethyl ether, di-tert-butyl ether, diglyme, dimethoxyethane, dimethoxymethane, methoxyethane, and mixtures thereof.

4. The process according to claim 3, wherein the solvent is selected from the group consisting of n-hexane, cyclohexane, toluene, dichloromethane, diisopropyl ether, tetrahydrofuran, and mixtures thereof.

5. The process according to claim 4, wherein the the solvent is selected from the group consisting of n-hexane, toluene, dichloromethane, tetrahydrofuran, and mixtures thereof.

6. The process according to claim 1, wherein the reaction mass is maintained in the process below −50° C.

7. The process according to claim 6, wherein the reaction mass is maintained at about −70 to −85° C.

8. A process for the preparation of 3-[3-(trifluoromethyl)phenyl]propionaldehyde, which comprises:
(a) reducing methyl 3-[3-(trifluoromethyl)phenyl]propanoate with diisobutylaluminium hydride (DIBAL-H) in an hydrocarbon solvent, an chlorinated solvent, an ether solvent or mixtures thereof below −40° C.;
(b) quenching the reaction mass with an alcohol solvent;
(c) adding ethyl acetate to the reaction mass obtained in step (b);
(d) separating out the solids; and
(e) isolating 3-[3-(trifluoromethyl)phenyl]propionaldehyde from the mother liquor.

9. The process according to claim 8, wherein the solvent used in step (a) is selected from the group consisting of cyclohexane, cyclohexene, cycloheptane, cyclopentane, n-hexane, n-heptane, benzene, toluene, xylene, dichloromethane, chloromethane, dichloroethane, chloroform, carbon tetrachloride, chlorobenzene, tetrahydrofuran, diisopropyl ether, tertrahydropyran, 1,4-dioxane, methyl tert-butyl ether, ethyl tert-butyl ether, diethyl ether, di-tert-butyl ether, diglyme, dimethoxyethane, dimethoxymethane, methoxyethane, and mixtures thereof.

10. The process according to claim 8, wherein the reaction mass is maintained in step (a) below −50° C.

11. The process according to claim 8, wherein the alcohol solvent used in step (b) is selected from the group consisting of methanol, ethanol, isopropyl alcohol, isobutanol, n-butanol, and mixtures thereof.

12. The process according to claim 11, wherein the alcohol solvent is methanol.

13. A process for the preparation of cinacalcet hydrochloride, which comprises:
(a) adding 3-[3-(trifluoromethyl)phenyl]propionaldehyde to (R)-(1-naphthyl)ethylamine in ether solvent in the presence of titanium(IV)isopropoxide below −5° C.;
(b) reacting sodium cyanoborohydride with the reaction mass obtained in step (a);
(c) concentrating the reaction mass;
(d) adding ether solvent, hydrochloride in an organic solvent and water to the residual mass obtained in step (c); and
(e) isolating cinacalcet hydrochloride.

14. The process according to claim 13, wherein the ether solvent used in step (a) and step (d) is independently selected from the group consisting of tetrahydrofuran, diisopropyl ether, tertrahydropyran, 1,4-dioxane, methyl tert-butyl ether, ethyl tert-butyl ether, diethyl ether, di-tert-butyl ether, diglyme, dimethoxyethane, dimethoxymethane, methoxyethane, and mixtures thereof.

15. The process according to claim 13, wherein the reaction in step (a) is carried out below −20° C.

16. The process according to claim 13, wherein the organic solvent used in step (d) is selected from the group consisting of an ether solvent, an ester solvent, and mixtures thereof.

17. A process for the purification of cinacalcet hydrochloride, which comprises:
   (a) stirring cinacalcet hydrochloride with a solvent system comprising water and solvent selected from alcohol solvent, nitrile solvent and mixture thereof; and
   (b) isolating substantially pure cinacalcet hydrochloride.

18. The process according to claim 17, wherein the alcohol solvent used in step (a) is selected from the group consisting of methanol, ethanol, isopropyl alcohol, isobutanol, n-butanol, and mixtures thereof.

19. The process according to claim 17, wherein the nitrile solvent used in step (a) is selected from the group consisting of acetonitrile, propionitrile, butyronitrile, benzonitrile, and mixtures thereof.

20. The process according to claim 17, wherein the step (a) is carried out at above 25° C.

\* \* \* \* \*

UNITED STATES PATENT AND TRADEMARK OFFICE
CERTIFICATE OF CORRECTION

PATENT NO. : 8,921,606 B2  
APPLICATION NO. : 13/810319  
DATED : December 30, 2014  
INVENTOR(S) : B. Reddy et al.

Page 1 of 1

It is certified that error appears in the above-identified patent and that said Letters Patent is hereby corrected as shown below:

In the specification,

Column 3, Lines 53, 54 and 55; and Column 4, Lines 53, 54, and 55 are missing due to PTO printing error.

Column 3; Lines 53, 54 and 55 should read as follows:

was also described in PCT publications WO 2008/035381, WO 2008/058235, WO 2008/117299; Tetrahedron Letters 2008 49(1), 13-15 and Synthetic communications 2008

Column 4; Lines 53, 54 and 55 should read as follows:

The present invention is intended to enhance the purity of cinacalcet hydrochloride. In particular, the present invention is directed to reduce or remove 2-[3-(trifluoromethyl)phe- In the claims, Column 12, Lines 54 and 55 (claim 13) are missing due to PTO printing error.

Column 12; Lines 54 and 55 (claim 13) should read as follows:

(a) adding 3-[3-(trifluoromethyl)phenyl]propionaldehyde to (R)-(1-naphthyl)ethylamine in ether solvent in the Signed and Sealed this  
Seventh Day of April, 2015

Michelle K. Lee  
*Director of the United States Patent and Trademark Office*